United States Patent [19]
Pranevicius et al.

[11] Patent Number: 6,105,582
[45] Date of Patent: Aug. 22, 2000

[54] CEREBRAL BLOOD OUTFLOW MAINTENANCE DURING INTRACRANIAL HYPERTENSION

[76] Inventors: Osvaldas Pranevicius; Mindaugas Pranevicius, both of 48-76-th St., Brooklyn, N.Y. 11209

[21] Appl. No.: 09/229,774

[22] Filed: Jan. 13, 1999

Related U.S. Application Data

[60] Provisional application No. 60/093,713, Jul. 28, 1998.

[51] Int. Cl.$^7$ .................................................. A61B 19/00
[52] U.S. Cl. ........................... 128/898; 604/505; 128/748
[58] Field of Search .................................... 128/748, 774, 128/898, 661.07, 661.1, 666–675; 604/8–10, 500, 503, 505

[56] References Cited

U.S. PATENT DOCUMENTS

| | | | |
|---|---|---|---|
| 4,204,547 | 5/1980 | Allocca | 128/748 |
| 4,621,647 | 11/1986 | Loveland | 128/748 |
| 4,648,384 | 3/1987 | Schmukler | 128/1 D |
| 4,850,969 | 7/1989 | Jackson | 604/96 |
| 4,917,667 | 4/1990 | Jackson | 604/96 |
| 5,183,058 | 2/1993 | Janese | 128/847 |
| 5,204,327 | 4/1993 | Kiyota et al. | 514/12 |
| 5,486,204 | 1/1996 | Clifton | 607/96 |
| 5,573,007 | 11/1996 | Bobo, Sr. | 128/748 |
| 5,579,774 | 12/1996 | Miller et al. | 128/667 |
| 5,676,145 | 10/1997 | Bar-Lavie | 128/634 |
| 5,683,357 | 11/1997 | Magram | 604/8 |
| 5,755,237 | 5/1998 | Rodriguez | 128/898 |
| 5,794,629 | 8/1998 | Frazee | 128/898 |
| 5,797,403 | 8/1998 | DiLoreno | 128/856 |
| 5,837,706 | 11/1998 | Shirasaki | 514/252 |
| 5,865,789 | 2/1999 | Hattler | 604/26 |

OTHER PUBLICATIONS

Rodbard, S., "Flow Through Collapsible Tubes. . .".

Rodbard S. Flow Through Collapsible Tubes: Augmented Flow Produced by Resistance at the Outlet. Circulation 9:280–287, Feb. 1955.

Conrad W.A. Pressure–Flow Relationships in Collapsible Tubes. IEEE Transactions on Bio–Medical Eng:BME 16.N.4., Oct. 1969:p. 284–295.

Yoku N, Tsuru M, Yada K. Site and Mechanism for Compression of the Venous System During Experimental Intracranial Hypertension. J. Neurosurg 41; p. 427–434, Oct. 1974.

Laas R, Arnold H. Compression of the Outlets of the Leptomeningeal Veins—the Cause of Intracranial Plateau Waves. Acta Neurochirurgica 58, 187–201, 1981.

Luce J M, Huseby JS, Kirk W, Butler J. A Starling Resistor Regulates Cerebral Venous Outflow in Dogs. J. Appl. Physiol. 53(6): 1496–1503, 1982.

Chopp M, Portnoy HD, Branch C. Hydraulic Model of Cerebrovascular Bed: An Aid to Understanding the Volume-–Pressure Test. Neurosurgery 13:5–11, 1983.

Asgeirsson B, Grände PO, Nordström CH. A New Therapy for Post–Trauma Brain Oedema Based on Haemodynamic Principles for Brain Volume Regulation. intensive care Med 20:260–267, 1994.

*Primary Examiner*—Mark O. Polutta
*Assistant Examiner*—William Noggle

[57] ABSTRACT

Method and apparatus for detecting and treating cerebral blood vessel collapse (54) during intracranial hypertension or vasospasm by affecting cerebral venous outflow pressure (61). Venous collapse is diagnosed by lowering jugular venous bulb pressure (61) and detecting significant, progressively increasing gradient between it and ICP (60). Rising jugular venous pressure initially the collapse is terminated and then ICP starts to increase. Increasing jugular venous pressure opens collapsed vascular segments by increasing intravascular pressure. There is no increase in ICP if jugular venous pressure is maintained below value that affects ICP. During life-threatening vascular collapse caused by a plateau wave or vasospasm venous outflow pressure is temporarily increased to a level necessary to terminate collapse regardless of ICP. This is accomplished by venous occlusion catheter placed into dominant jugular vein. Catheter has highly compliant inflatable balloon operating like Starling resistor for venous outflow pressure control. Quick control of venous pressure is achieved by withdrawing/injecting fluid through catheter tip. Operation catheter is controlled by controller, which also measures ICP and possibly CBF, $S_{jv}O_2$. Alternative venous outflow control measures are possible.

3 Claims, 11 Drawing Sheets

CEREBRAL BLOOD OUTFLOW MAINTENANCE DURING INTRACRANIAL HYPERTENSION

BACKGROUND -- Cross-References to Related Applications

This application claims the benefit of Provisional Pat. application Ser. No. 60/093,713, filed Jul. 28, 1998.

BACKGROUND -- Field of Invention

This invention relates to blood flow control in organs with increased compartmental- tissue pressure and collapsible vessels, specifically in the brain.

BACKGROUND -- Description of Prior Art

The concept of critical cerebral blood flow (CBF) under the conditions of increased intracranial pressure (ICP) are well known (1,2). Studies have correlated specific levels of regional cerebral blood flow (rCBF) with reproducible clinical end points such as EEG slowing up to the point of isoelectricity. Normal rCBF of 40–60 mL/100 g/ min will maintain ion pumps, membrane potential, and the overall cellular energy pool (3). Cellular electrical failure occurs at rCBF of 15 mL/ 100 g/min (2). Decrements in rCBF below this level do not correlate with clinical end points and associated with an adverse outcome (2). From an energy standpoint, rCBF <10–12 mL/100 g/min does not support aerobic metabolism. Anaerobic glycolysis becomes predominate source of adenosine triphosphate (ATP) synthesis and intracellular acidosis steadily develops through the enhanced generation of lactate (4) If untreated, CBF <10 mL/100 g/min will induce a cascade of metabolic events, ultimately leading to cellular death. This is the CBF threshold for energy and ion homeostasis below which cellular death invariably occurs (2).

On the other hand cerebral perfusion pressure (CPP) is directly affected by ICP, because cerebral veins are exposed to cerebrospinal fluid (CSF) and passively collapse following an elevation of ICP (5). In the case of significant ICP elevation and following intracerebral vein collapse and CPP drops below its autoregulatory limits. That causes cerebral perfusion to be passively dependent from mean arterial pressure (6). Further increase in ICP ceases CBF entirely (5,7,8,9,10,11,12).

Presently available treatment modalities aim to decrease ICP and maintain CBF during intracranial hypertension (6,13,14,15). All of them suffer from a number of disadvantages:

(a) Cerebral blood flow during intracranial hypertension is maintained by preserving high CPP (above 70–80 mmHg) (6,16,17). That necessitates positive inotropic support. That results in side effects such as myocardial ischaemia, peripheral organ hypoperfusion and elevation of ICP (16,17).

(b) Besides diuretic therapy, non-surgical methods to reduce CBF and ICP include high dose barbiturates and hyperventilation (18). Barbiturates decrease cerebral metabolic rate and CBF in proportion to that, what is attributed to their protective effect. Still some studies showed limited effectiveness of barbiturates and complications related to this therapy such as arterial hypotension and myocardial depression what by itself might cause cerebral hypoperfusion (16,19,20). Hyperventilation decreases ICP at the expense of cerebral vasoconstriction. Thus CBF is reduced and can cause ischaemia (21). Prolonged use of hyperventilation causes rebound vasodilatation (7), so this therapy can serve only as temporary measure.

(c) CSF drainage through ventricular catheter is limited to situations when ventricles are not collapsed. Drainage itself can cause ventricular collapse and cerebral displacement.

(d) Osmotic diuretic therapy is the mainstay of therapy in many centers (18). Interrupted CBF allows osmotic molecules to penetrate in to the brain tissue and can diminish fluid absorption. Also discontinuing long-term infusion causes rebound increase of ICP (22).

(e) Surgical treatment of intracranial hypertension includes removal of mass lesions and decompressive craniotomy. It is limited to the extreme and resistant cases and has all the limitations inherent to any extensive surgical procedure.

In summary present methods of treatment include maintaining CPP, lowering ICP and lowering cerebral metabolic rate. All of them are limited to a specific clinical context and their efficacy on outcome is questioned (23). None of these methods considers cerebral vascular collapse as the mechanism by which ICP elevation causes cerebral hypoperfusion nor is directed to minimize the effect of increased ICP on the vascular collapse.

OBJECTS AND ADVANTAGES

An object of our invention is a control of collapsibility factor in the cerebral vasculature. We therefore deemed it pertinent to review basic physiological effects, related to collapsibility of intracranial vessels, before discussing the advantages of our invention.

Figure 5:
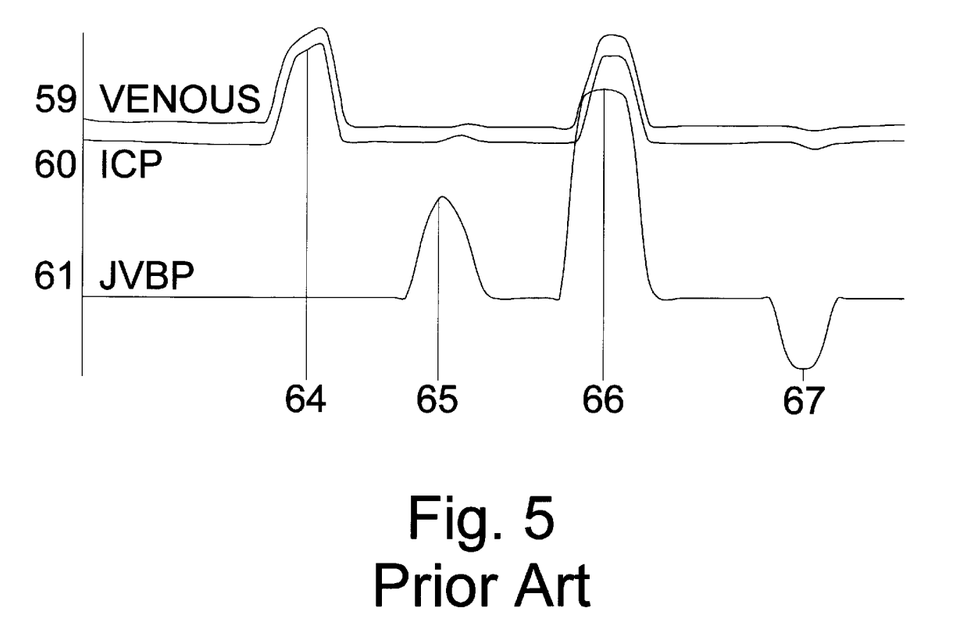
FIG. 5 shows schematic relationship between ICP, cerebral venous pressure (CVP) and jugular venous bulb pressure (JVBP).

Experimental physiological data indicate that intracerebral vein pressure 59 is slightly above ICP 60 (24,25). However dural sinuse pressure is lower than that in the veins and not related to ICP (24, 25). FIG. 5 shows that spontaneous increase in ICP does not affect jugular vein bulb pressure (JVBP) 64. Small JVBP increase does not affect ICP either 65. Higher increase of JVBP rises both cerebral venous pressure 59 and ICP 60 to the equal extent. JVBP drop 67 does not affect ICP or cerebral venous pressure (24). This leads to an interesting physiological phenomenon called "vascular waterfall." When this happens, flow rate through a collapsible tube will depend only on an upstream pressure at the feeding and will be independent of downstream pressure at the exit end. This is in a sharp contrast to ordinary laminar or turbulent flow in rigid pipes, where flow is proportional to the pressure gradient between the entry and exit ends. This behavior is similar to that of a mountain waterfall, flow rate of which depends on the quantity of flow at the source and not on the height of fall. In physiology this is the principle of Starling resistor- a flexible rubber tubing used for peripheral resistance by E. H. Starling in his first heart-lung preparation (26).

Figure 4A:
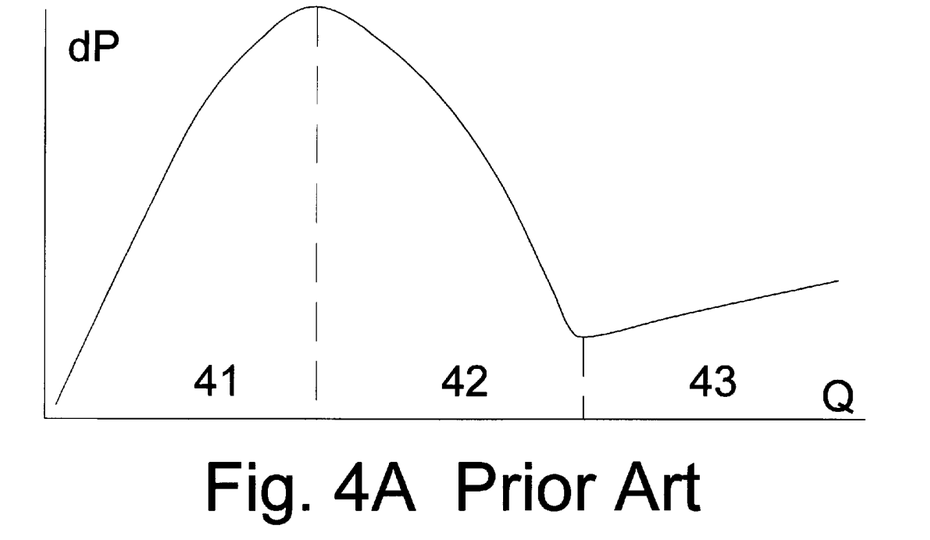
FIGS. 4A and 4B show flow Q and perfusion pressure dP relationship in collapsible tube and corresponding shape of collapsible tube.
Figure 4B:
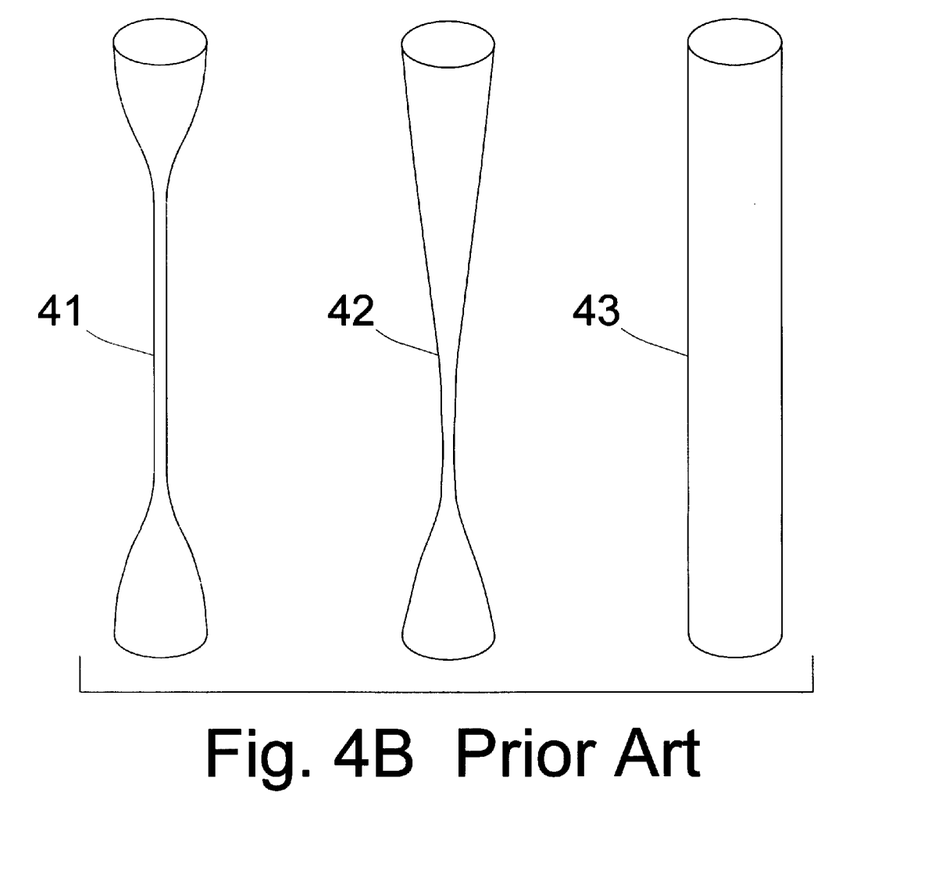

Analysis of vessel collapse shows that under some circumstances provision of resistance to the outflow end might actually enhance flow through a collapsed tube segment (27). This is because distal resistance increases distending pressure on the collapsed segment, and by that eliminate the most effective hindrance to flow such as progressive and recurrent narrowing of the collapsed segment. This effect originates from a fact that collapsible tubes have an unequivocal and nonlinear flow (Q)-pressure (P) interrelationship. When transmural pressure (Ptm) is positive, cerebral veins assume circular cross-shape 43. If during intracranial hypertension ICP exceeds venous pressure, the vein wall is subjected to circumferential compression with subsequential diminution of their cross-sectional area 42 and full collapse 41. Between fully distended 43 and fully collapsed 41 state veins exhibit highly nonlinear and unequivocal P-Q interrelationship (FIG. 4A), part of which (when veins are partially collapsed 42) is inverted. In this part flow through the vein increases as pressure gradient along it falls (FIG. 4A 42). In other words it is possible to augment CBF by decreasing an extra-intracranial pressure gradient (by opening closed Starling resistor). This is the physiological basis for reestablishing CBF, hindered by an increased ICP.

It has direct relationship to the "plateau waves"- spontaneous and acute elevations of ICP rapidly rising above an elevated baseline level. These elevations of ICP may reach 50 to 100 mmHg and last any time from 2–3 minutes to 20–30 minutes (8,28). They are associated with worsening neurological status. Clinically at its peak, plateau wave presents with apnea, respiratory arrest, decerebration and marked depression in level of consciousness (28). Human studies have shown them to be associated with a progressive increase in CBV, diminished CBF and CPP—all of which tended to be greatest just before the termination of wave (9). Analysis of the possible plateau wave causes shows their direct relationship to the cerebral vein collapse or "Starling resistor" (11). Accordingly to this scheme, flow through the cerebral veins is dependent exclusively on ICP surrounding veins once ICP exceeds sagital sinus pressure. The later is not affected by ICP because of the unyielding sinus walls. The thin-walled cerebral veins and lacunae are exposed to intracranial fluid. On the other hand, intraluminal pressure in sinus is much lower than ICP. Venous blood drains into sinus through the lacunae whose walls are collapsible and therefore require an upstream cerebral venous pressure to be slightly above ICP (24,29). When ICP increases to a degree sufficient to cause partial collapse of the lacunae, cerebral venous outflow is impeded (34,35). Subsequently CBV and ICP increase ("Starling resistor" closes). By "opening Starling resistor", we suggest possibility to reestablish intracranial circulatory conditions.

There have been multiple experimental and clinical studies showing safety and possible effectiveness of the method described below.

Junichiro Kotani while studying effect of cerebral venous congestion on the pressure-volume index found paradoxical improvement in intracranial pressure buffering capacity against the volume load under the conditions of sagital sinus hypertension (25).

Wagner EM at al. found that cerebral venous pressure elevation to approximately 16.0 mmHg decreases cerebral venous outflow to 40% of control value with no effect on total and regional CBF values (30).

Paul J. Chai found that ligation of right jugular veins does not increase intracranial pressure, but increase CBF and cerebral oxygen consumption (31).

Basil Matta et all described a case of previously healthy 24-year-old man after the head injury in whom Valsalva maneuver at the peak of a spontaneously developing plateau wave resulted in complete abortion of the wave and spontaneous reduction of ICP (32). At the times when neurosurgical procedures used to be performed with the patient in a sitting position, direct jugular venous compression (as prophylactic measure against venous air embolism) even with the pressures as high as 140 mmHg proved to be safe and did not significantly increased ICP (33).

John M. Luce found that under the conditions of intracranial hypertension, elevation of the sagital sinus pressure does not cause significant increase in ICP (24).

Accordingly several objects and advantages of our invention are:

(a) It maintains cerebral venous flow under the conditions of intracranial hypertension by dynamically controlling outflow pressure in a way that venous collapse is prevented, but ICP is not altered.

(b) It avoids all complications of the current treatment modalities such as myocardial ischaemia, hypoperfusion of peripheral organs, excessive cerebral vasoconstriction, cardiovascular depression and fluid - electrolyte disorders.

(c) It complements present methods of treatment by directly treating intracranial vascular collapse.

(d) Combination of the present treatment methods to decrease ICP and prevention of the cerebral vascular collapse under the conditions of increased ICP can significantly improve management and outcome in neurological intensive care.

Further objects and advantages of our invention will become apparent from a consideration of the drawings and ensuing description.

DRAWING FIGURES

In the drawings closely related figures have the same number but different alphabetic suffixes.

Reference Numerals in Drawings

| | |
|---|---|
| 12 jugular venous occlusion catheter | 56 jugular vein bulb |
| | 58 pressure in arteries |
| 14 pump controlling balloon pressure | 59 pressure in cerebral veins |
| | 60 intracranial pressure |
| 16 reservoir connected to balloon | 61 jugular vein bulb pressure |
| 18 pump for infusion/withdrawing fluid trough catheter tip | 62 pressure in inflatable balloon |
| | 64 spontaneous increase in ICP |
| 20 ICP probe | 65 JVBP increase not affecting ICP |
| 22 controller | |
| 24 computer | 66 higher JVBP increase causes ICP to rise |
| 26 main lumen of catheter | |

-continued

| Reference Numerals in Drawings | |
|---|---|
| 28 catheter tip | 67 JVBP drop does not affect ICP |
| 30 balloon lumen | |
| 32 inflatable balloon | 68 balloon inflated |
| 34 optic fiber for measuring $S_{JV}O_2$ | 69 JVBP response to balloon inflation |
| 36 thermistor for CBF measurement | |
| 41 zone of complete tube collapse | 70 bolus injected through catheter tip |
| 42 zone of partial tube collapse | |
| 43 zone of opening of collapsible tube | 71 JVBP response to bolus injection |
| 44 scull | 72 bolus withdrawn through catheter tip |
| 46 brain | |
| 48 cerebrospinal fluid | 73 JVBP response to bolus withdrawal |
| 50 cerebral arteries | |
| 52 capillaries | 74 balloon deflated |
| 53 cerebral veins | 75 JVBP response to balloon deflation |
| 54 collapsible veins | |
| | 77 JVBP reaches target JVBP1 |
| | 78 JVBP reaches target JVBP2 |
| | 80 ICP follows JVBP drop |
| | 82 spontaneous plateau wave of ICP |

SUMMARY

In accordance with the present invention a method of detecting and treating cerebral vessel collapse includes changing pressure in the venous outflow tract then assessing the impact of that change. Based on what presence or absence of cerebral vascular collapse is detected. Manipulation of cerebral venous outflow pressure is performed in such a way so that vascular collapse is prevented or aborted without increase in intracranial pressure.

Figure 1:
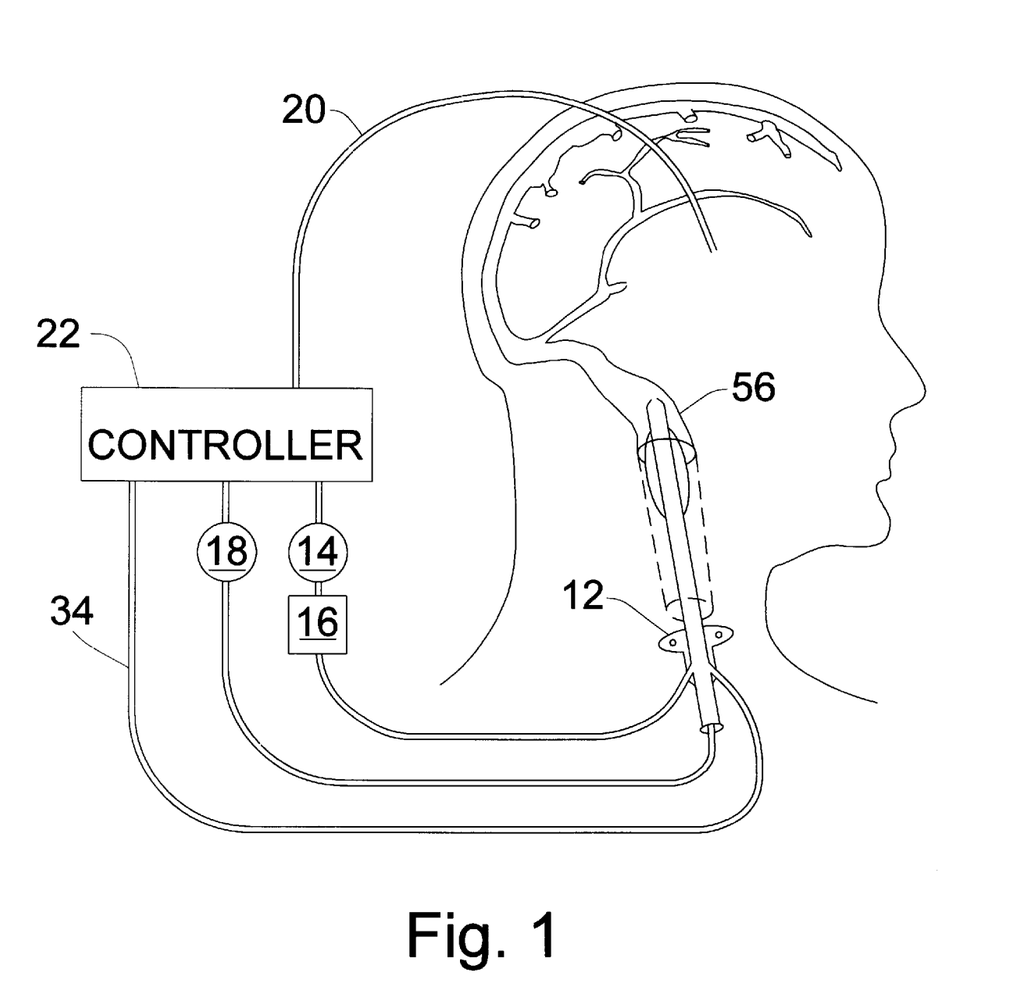
FIG. 1. shows apparatus for cerebral blood outflow control
Figure 2:
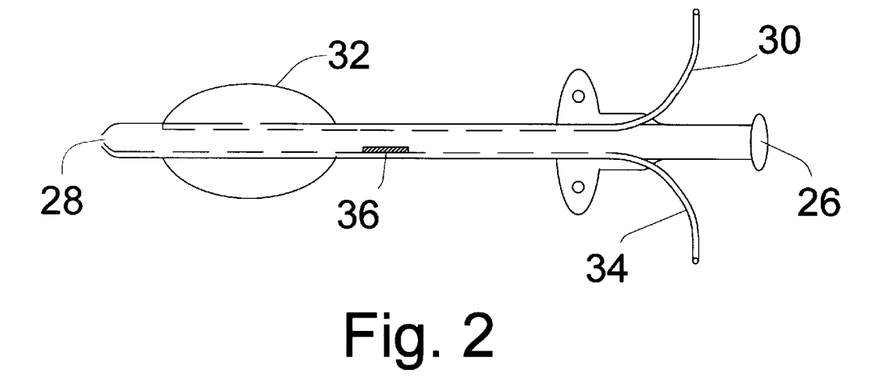
FIG. 2 shows jugular vein occlusion catheter with inflatable balloon.
Figure 3:
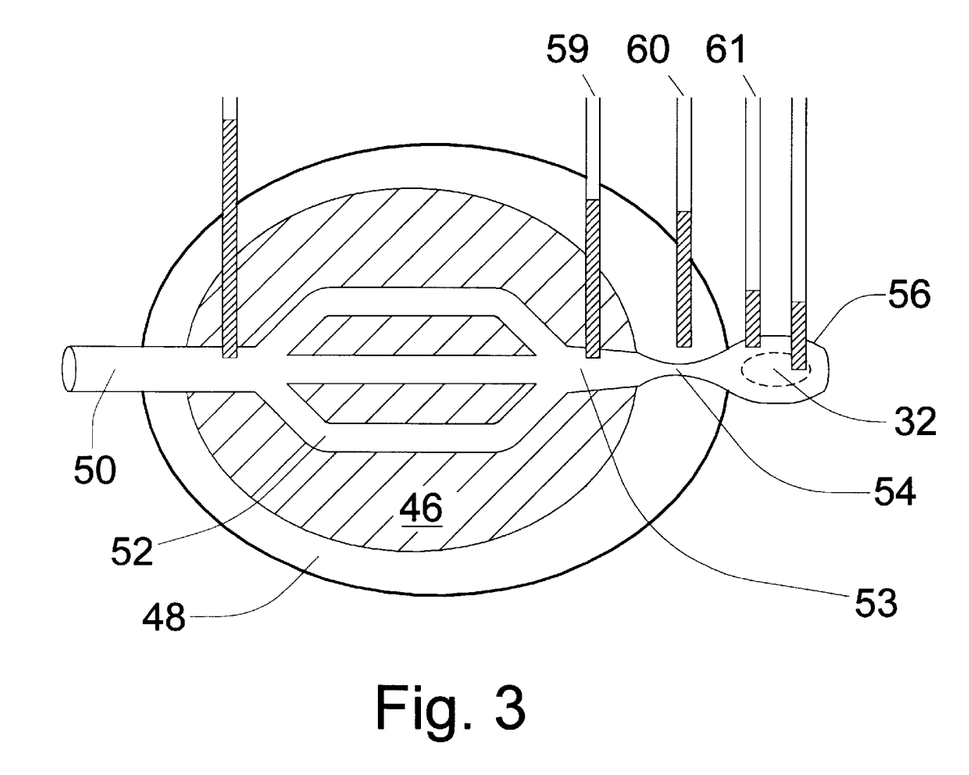
FIG. 3 shows schematic model of cerebral circulation and vascular pressures in presence of venous collapse.

DESCRIPTION - FIGS. 1–3

A typical embodiment of the present invention is illustrated in FIGS. 1 and 2.

FIG. 3 is a diagrammatic view of cerebral veins with dynamical occlusion apparatus in jugular vein bulb.

Cerebral venous pressure control apparatus includes jugular venous occlusion catheter 12 having its distal end inserted into the jugular vein bulb 56. The proximal end of catheter has a balloon inflation lumen 30 connected via reservoir 16 to the pump 14. Main lumen 26 connects to controller 22 for sensing jugular bulb pressure and fluid infusion/withdrawal pump 18. Preferential optic fiber 34 connects to controller 22 for measuring $S_{JV}O_2$. Preferential thermistor 36 connects to controller 22 for measuring CBF. Conventional ventricular ICP probe 20 connects to controller for ICP measurement. Controller 22 connects to pump 14 for balloon pressure control and to pump 18 for the fluid infusion/withdrawal through a catheter tip 28.

FIG. 2 is a diagrammatic view of the venous occlusion catheter 12. It has a length sufficient to extend from an insertion point to the jugular bulb, preferably 18 cm. The outer diameter of the catheter is less than the inner diameter of a jugular vein (range 4.5–5.5 Fr). The catheter is preferably opaque to X-rays and may be marked at the tip for easy visualization using conventional X-ray equipment. The catheter has at least two lumens, main lumen 26 opening at the tip of the catheter 28 and balloon lumen 30 forming low resistance connection between inflatable balloon 32 and pump 14 via the reservoir 16. Inflatable balloon is preferably made from a highly compliant or easily folding material, so that balloon 32, low resistance balloon channel 30 and reservoir 16 together form the high compliance system filed with a low viscosity gas, preferably helium. The catheter preferably incorporates a conventional optic fiber 34 for the oxygen saturation measurement in the jugular bulb ($S_{JV}O_2$). The catheter preferably further incorporates a thermistor 36 positioned close to the catheter tip 28 and proximally to the balloon 32 for cerebral blood flow (CBF) measurement. Main lumen of the catheter 26 is connected to the controller 22 for jugular vein bulb pressure sensing. Alternatively jugular vein bulb pressure can be sensed through conventional fiberoptic pressure sensor. Main catheter lumen 26 is also connected to the pump 18 for fluid injection/withdrawal.

FIG. 3 is diagrammatic view of the cerebral circulation with jugular venous occlusion balloon 32 placed in the jugular vein bulb 56. This scheme shows arteries 50 penetrating brain substance 46 then dividing into capillaries 52 that merge into cerebral veins 53 then go from the brain substance into superficial collapsible veins 54, the latter being directly exposed to cerebrospinal fluid 48. Superficial collapsible veins 54 drain into jugular vein bulb 56 through rigid sinuses.

OPERATION -- FIGS. 1, 2, 4–11B

Figure 6A:
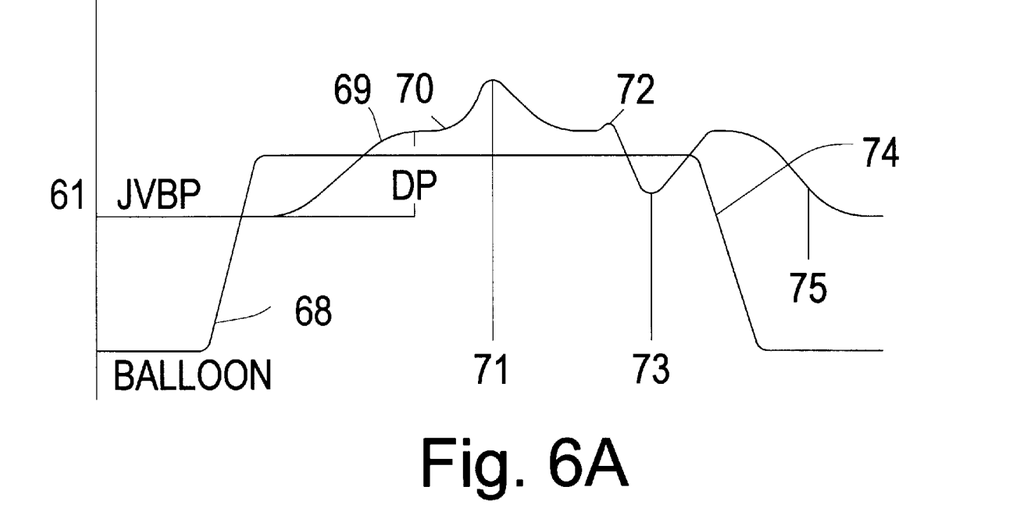
FIGS. 6A and 6B show jugular vein bulb pressure response to occlusion and bolus injection.

Installation- FIGS. 1, 3. Conventional ICP probe 20 is connected to controller 22 calibrated to measure ICP. Dominant jugular vein is determined in a usual fashion (larger opening on X-ray film or higher ICP response to vein compression). Jugular vein occlusion catheter 12 is flushed and percutaneously placed in the dominant jugular vein using Seldinger over the wire technique. Catheter tip 28 position in the jugular vein bulb is confirmed with a conventional imaging technique. Balloon lumen 30 is connected to the balloon pressure control pump 14 via the reservoir 16. Main catheter lumen 26 is connected to pump 18 for fluid injection/withdrawal. Main catheter lumen 26 or special channel for measuring jugular vein bulb pressure (JVBP) is connected to controller 22. In addition to controller 22 are connected: fiberoptic sensor 34 to measure $S_{JV}O_2$, and thermistor 36 to measure CBF. Initial ICP, JVBP, CBF, $S_{JV}O_2$ are assessed. If an increase in ICP together with CBF decrease is found outflow control is employed as follows. FIGS. 6A and B show JVBP response to balloon inflation and fluid injection withdrawal.

Figure 6B:
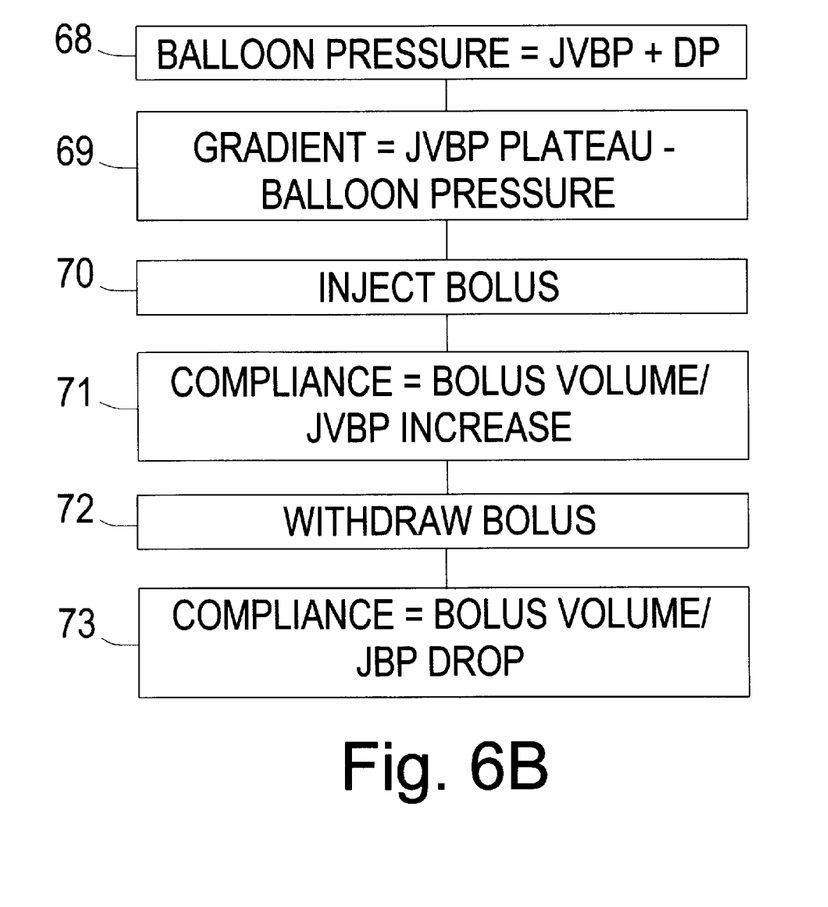

At the point 68 pump 14 increases balloon 32 pressure higher than baseline JVBP by a magnitude of DP. Balloon partially occludes internal jugular vein (IJV) and causes gradual JVBP rise, up to the point of plateau 69. JVBP response is assessed for [Lag time]=[time of JVBP plateau]-[time of balloon inflation] and [Balloon gradient]=[JVBP plateau]- [Pballoon]. The blood flowing around collapsible balloon determines said balloon gradient. After JVBP reaches plateau at 69, controller activates pump 18 to inject bolus of fluid into IJV 70. It causes almost simultaneous JVBP increase 71. Internal jugular vein [compliance]=[bolus volume]/[JVBP increase]. After JVBP reaches plateau again, controller activates pump 18 to withdraw bolus from IJV 72. This again causes drop in JVBP 73 and subsequential equilibration. IJV [compliance]=[bolus volume]/[JVBP drop] is estimated again. Then balloon is deflated 74 and JVBP returns to baseline 75.

Figure 7A:
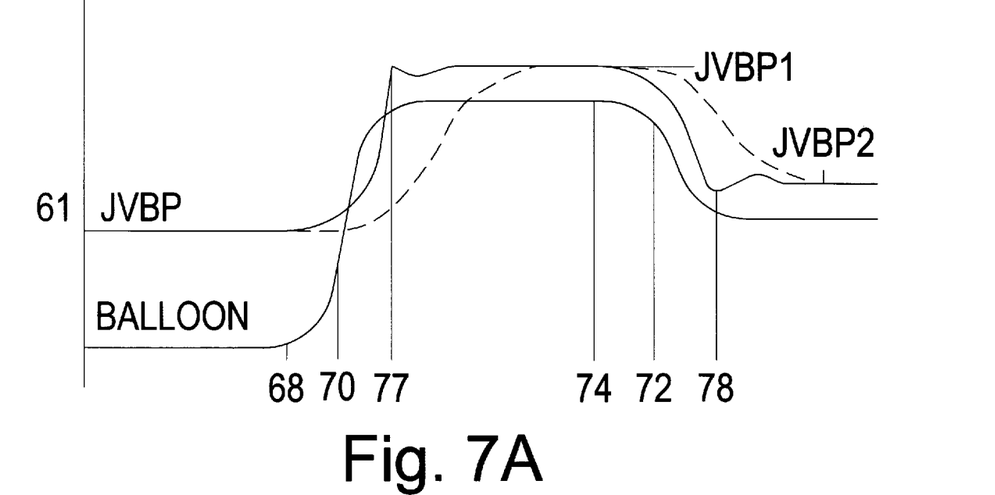
FIGS. 7A and 7B show JVBP control protocol.
Figure 7B:
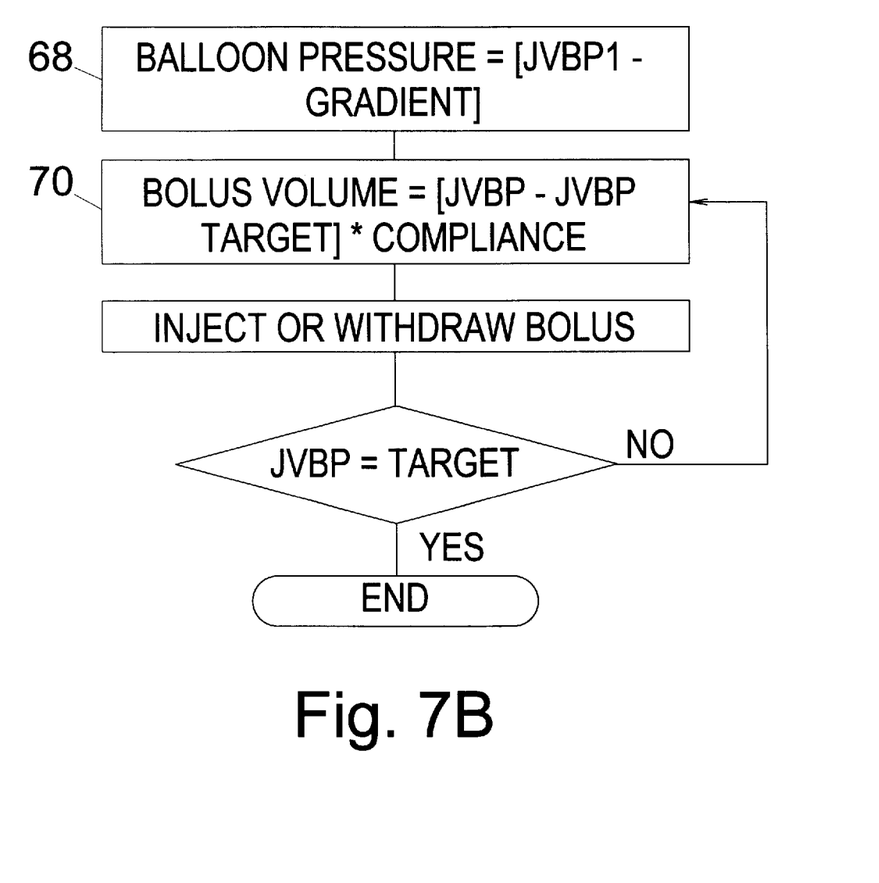

Estimated parameters- JVBP response [Lag time] after balloon inflation, [Balloon gradient] and [IJV compliance] are stored in controller 22. JVBP control function is based on these parameters as shown in FIGS. 7A and 7B.

To increase jugular vein bulb pressure to JVBP1 from the baseline balloon is inflated 68 to the pressure level

[Pballoon]=[JVBP1]- [Balloon gradient]. To shorten lag time, bolus of fluid is injected 70. [Bolus volume]=[IJV compliance]* [JVBP1-JVBPbaseline]. JVBP reaches JVBP1 at 77 as a result of balloon inflation and bolus injection. If bolus is not injected, lag time passes until JVBP reaches JVBPL as shown by the dot line. Procedure can be repeated to fine tune JVBP control if necessary.

To decrease JVBP from JVBP1 to JVBP2, pump 14 lowers balloon pressure to the level [Pballoon]=[JVBP2]-[Balloon gradient]78. Then pump 18 withdraws bolus 72. [Bolus volume]=[IJV compliance]X [JVBP-JVBP2]. That causes JVBP to reach JVBP2 78.

Dotted line shows JVBP response to balloon inflation and deflation without the fluid boluses. Note prolonged lag time until JVBP reaches the target level.

Figure 8A:
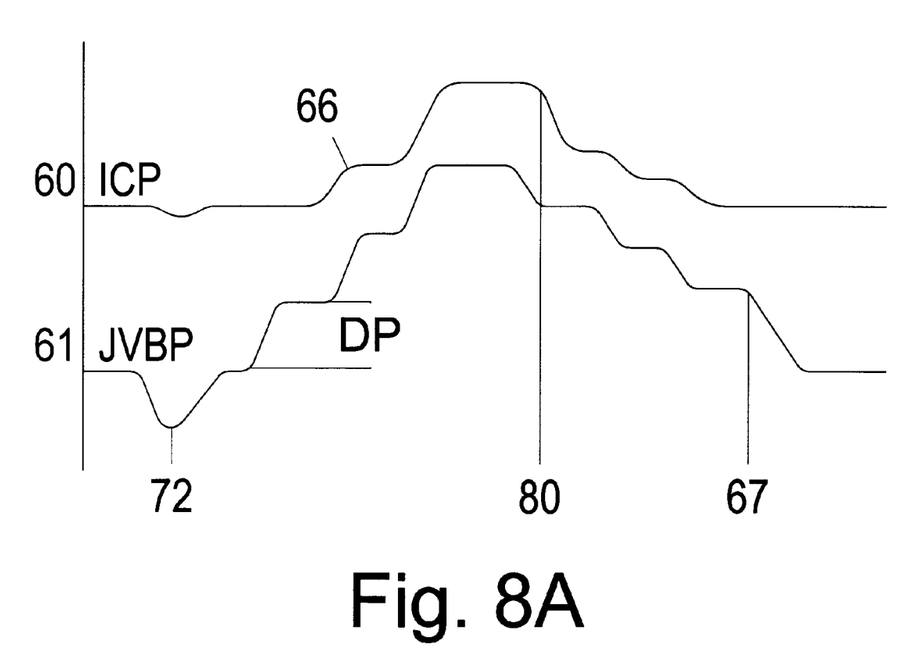
FIGS. 8A and 8B show ICP response to changes in JVBP and protocol to find safe gradient between ICP and JVBP, when JVBP does not affect ICP.
Figure 8B:
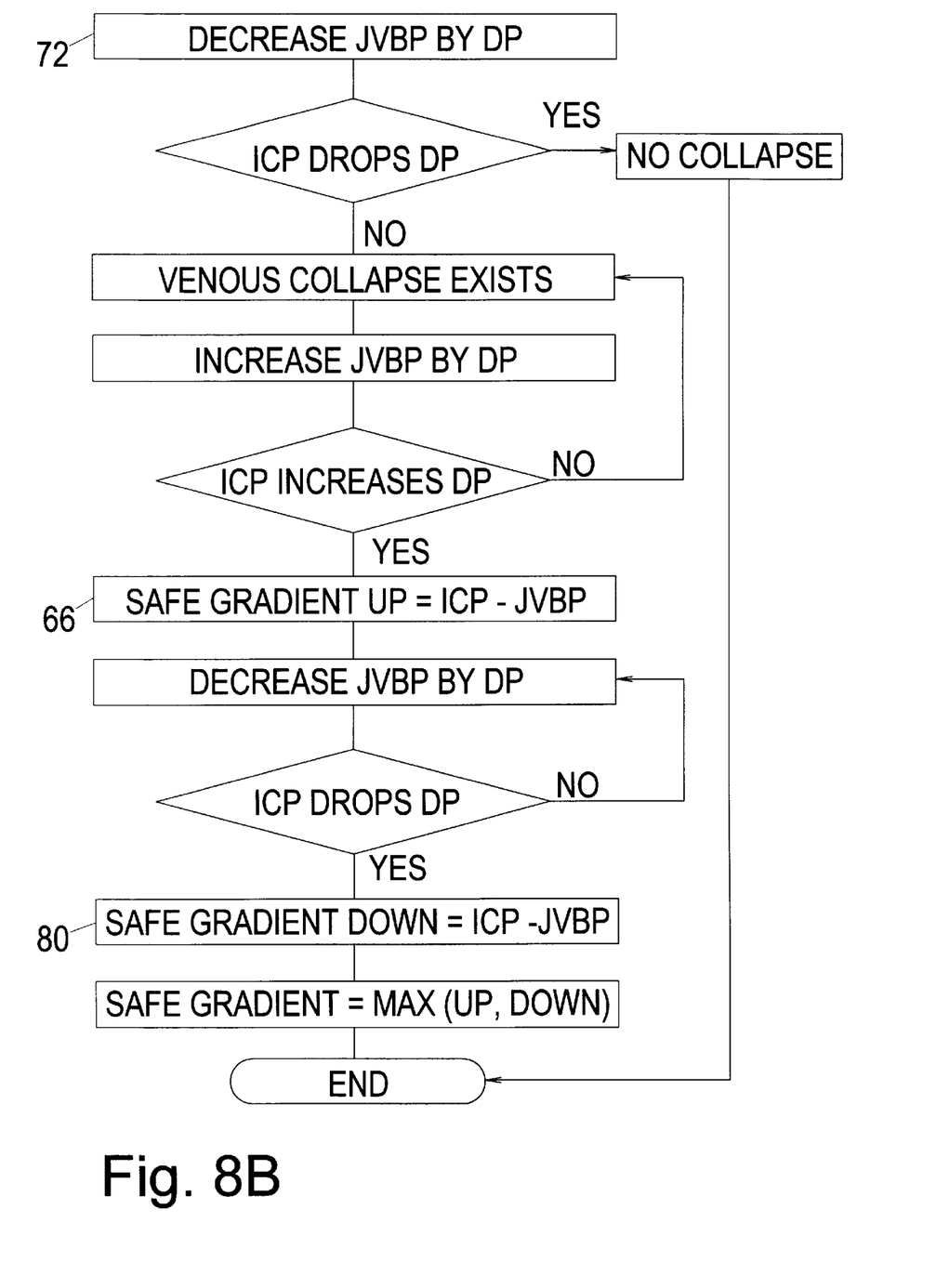

FIGS. 8A and B show an assessment of ICP/JVBP gradient. Initially pump 18 lowers JVBP by withdrawing bolus 72. If cerebral veins are collapsed ICP does not drop. Then JVBP is raised in a stepwise manner by the magnitude of DP at a time. At the point 66 when further JVBP increase cause ICP to rise, ICP/JVBP gradient [dPup=ICP-JVBP] is measured. Then JVBP is lowered in a stepwise manner by the magnitude of DP at a time. JVBP decrease cause ICP to decrease and the same gradient [dPdown]=[ICP-JVBP] is measured 80. Usually dPup and dPdown are approximately equal and represent pressure gradient between the collapsed cerebral veins and jugular vein bulb (JVB). Decreasing JVBP further, this gradient remains stable and ICP follows JVBP up until 67. From this point further drop of JVBP does not result in ICP decrease. This is the point when blood flow is limited by the cerebral veins collapse. It is described as Starling resistor or vascular waterfall. In order to manipulate JVBP without affecting ICP the difference between ICP and JVBP must always remain higher than ICP/JVBP gradient. This "safe gradient" is determined as dPsale=Max (dpup, dPdown)x110%. It is stored in the controller 22 and periodically reassessed.

Figure 9A:
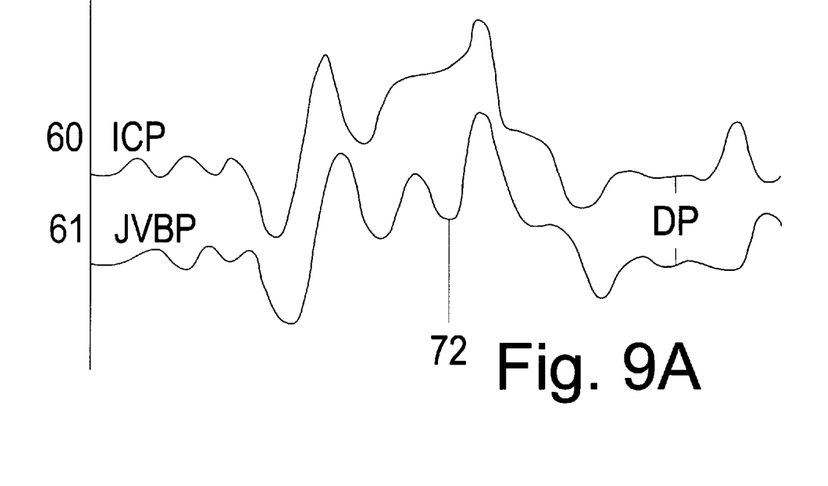
FIGS. 9A and 9B show JVBP and ICP when employing protocol to prevent venous collapse.
Figure 9B:
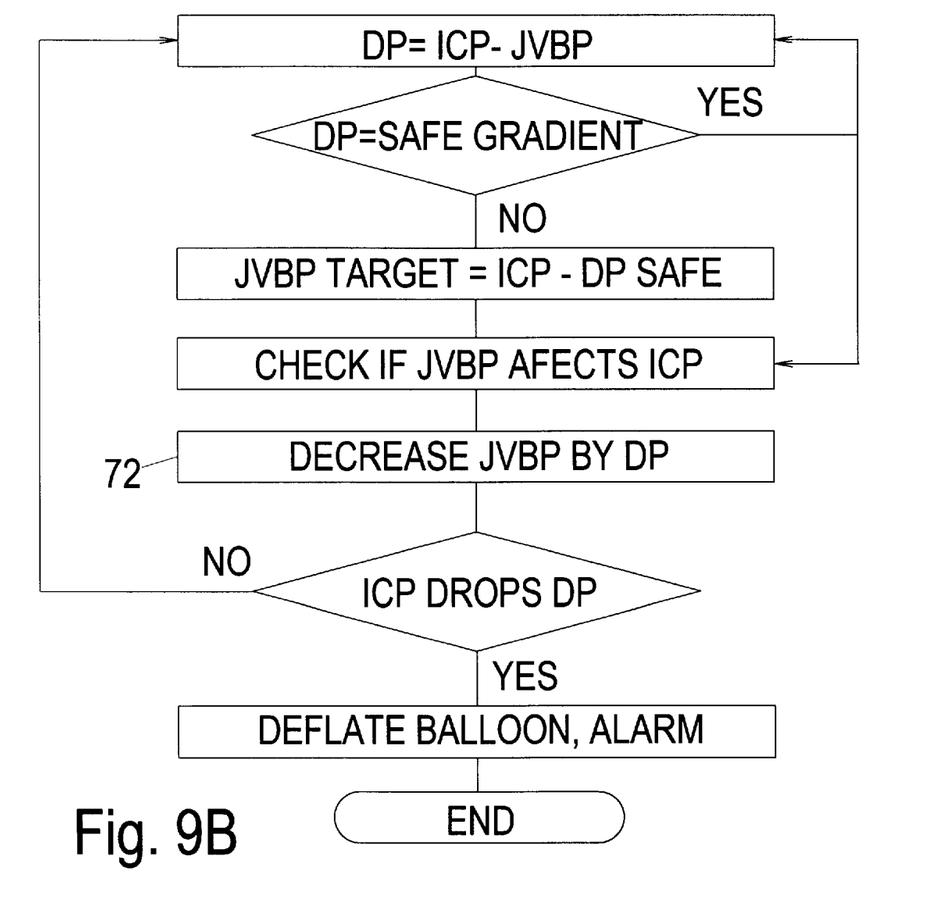

FIGS. 9A and B show protocol to maintain ICP-JVBP gradient to prevent venous occlusion.

Controller activates pumps 14 and 18 (inflating/deflating balloon and injecting/withdrawing fluid boluses) according to JVBP control function to maintain JVBPtarget=ICPfactual-dPsafe in real time. In a sense JVBP is maid to follow ICP. By controlling JVBP in this manner ICP is not affected however cerebral veins are maintained in an open state what improves CBF and decreases incidence of plateau waves. To ensure that ICP is not affected JVBP is periodically lowered withdrawing bolus of blood 72. Under the normal operating conditions there is no ICP response to this maneuver. However if ICP drops, for the safety reasons balloon is deflated and alarm is activated as shown in flowchart 9B. Effectiveness of control is periodically assessed using thermodilution to measure CBF and continuously monitoring $S_{JV}O_2$.

Figure 10A:
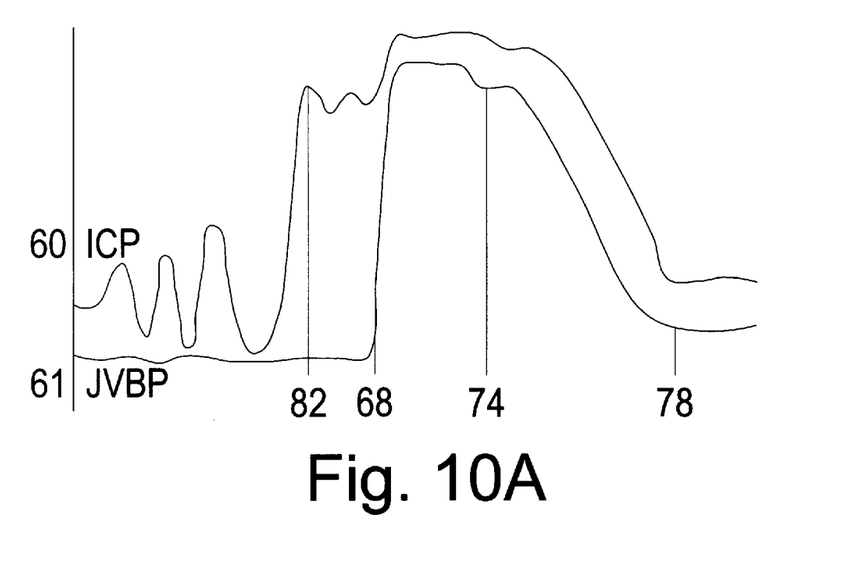
FIGS. 10A and 10B show JVBP and ICP when employing protocol to terminate plateau wave.
Figure 10B:
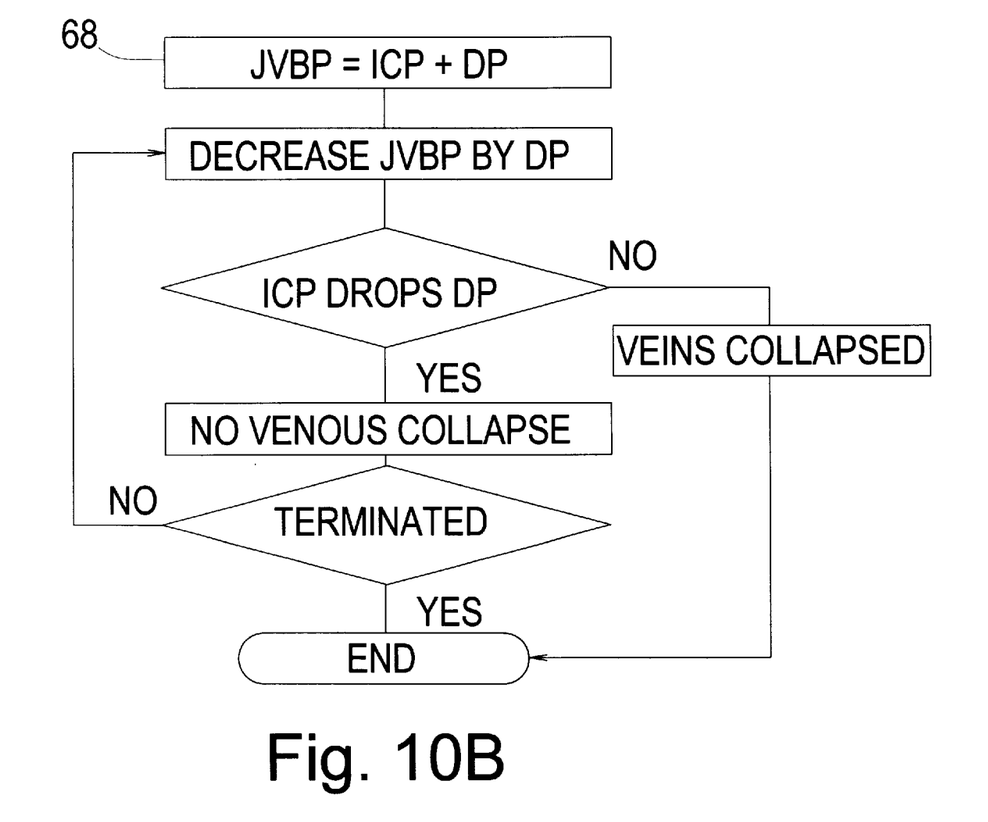

FIGS. 10A and 10B show protocol to terminate plateau wave. During plateau wave cerebral veins are fully collapsed 41 FIGS. 3A and B. ICP reaches extremely high level and impedes CBF 82. To interrupt such occlusion, balloon 32 is inflated 68 and fluid bolus is injected by the pump 18 to achieve JVBPtarget=ICPfactualx110%. It opens collapsed cerebral veins at expense of the further ICP increase. After this maneuver JVBP is lowered in a stepwise manner by the magnitude of DP at a time 74. If ICP drops by the magnitude of DP as well, this means that collapse is terminated and JVBP can be lowered further to baseline 78. If on the other hand ICP does not drop, it means that veins are still collapsed. Rising venous pressure higher to terminate collapse is considered. This way ICP plateau wave in progress can be terminated and CBF can be reestablished.

Figure 11A:
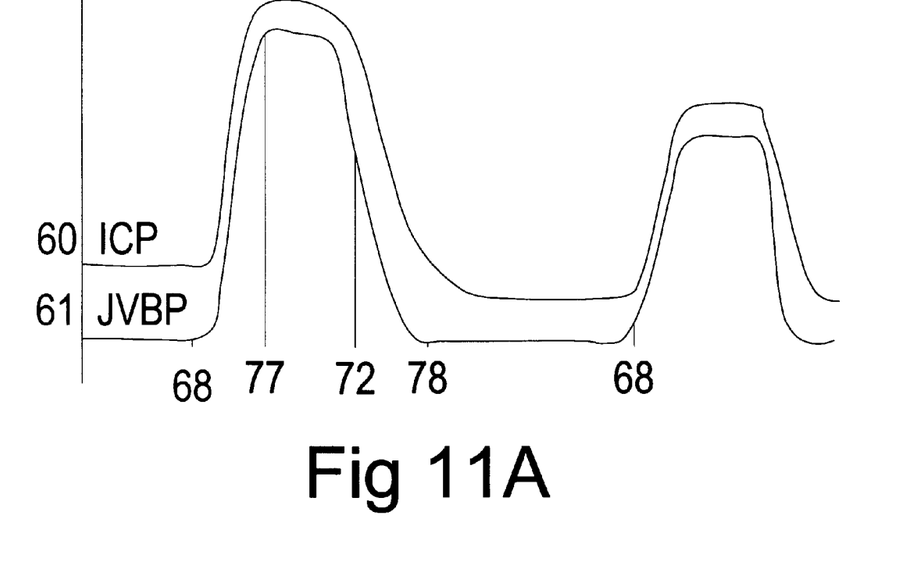
FIGS. 11A and 11B show JVBP and ICP when employing protocol to terminate precappillary vasospasm.
Figure 11B:
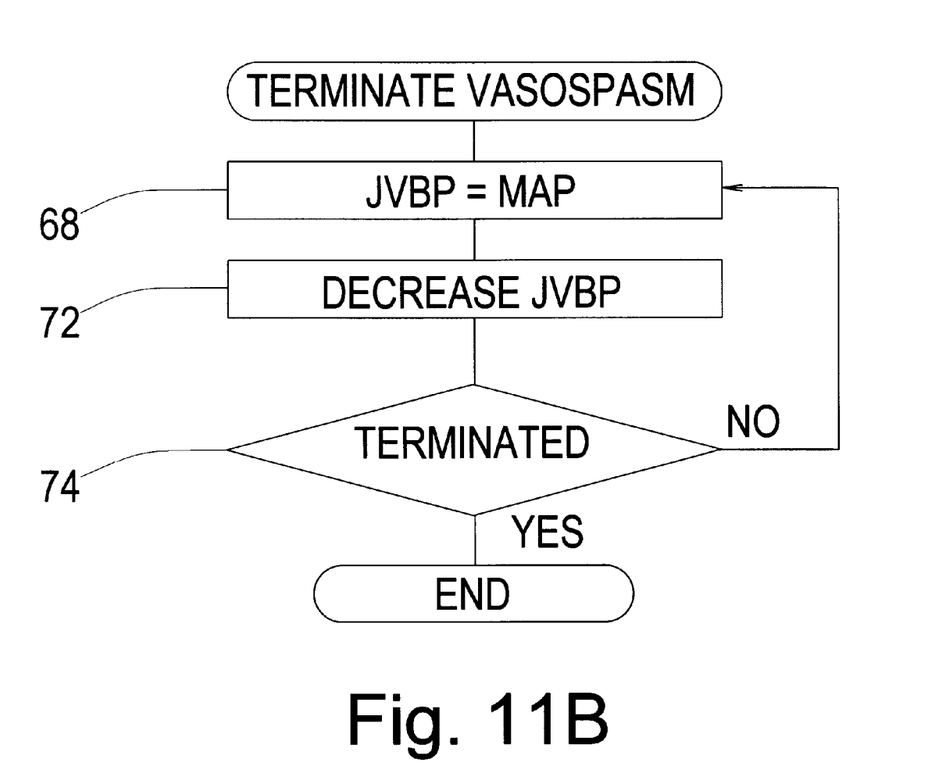

FIGS. 11A and B show protocol to terminate cerebral vasospasm. During arterial vasospasm precapillary sphincters are collapsed and CBF is significantly diminished. Accordingly to the Laplace law much higher pressure is needed to open collapsed vessel with small radius than to maintain already open vessel with larger radius. An attempt to break vasospasm from arterial side has limited success because only fraction of arterial pressure increase is transmitted to precapillary sphincters. On the other hand venous pressure increase is entirely transmitted to precapillary sphincters. To terminate vasospasm JVBP is increased close to mean arterial pressure 68 for a short period of time. This opens precapillary sphincters. ICP rises temporarily 77. Then lowering JVBP to baseline 72 restores flow and ICP gradually returns to baseline as well 78. Even with a lower transmural pressure precapillary sphincters will stay open because accordingly to the Laplace law (higher radius requires higher tangential wall tension to collapse the vessel). Effect is periodically assessed by CBF and $S_{JV}O_2$ measurements. This treatment can be repeated until vasospasm resolves.

CONCLUSION, RAMIFICATIONS, AND SCOPE

Potential use of cerebral venous outflow control:

1) To prevent cerebral venous collapse and outflow obstruction during acute or chronic intracranial hypertension, especially when it is accompanied with plateau waves and deteriorating neurological function.

2) To treat normal pressure hydrocephalus if venous outflow etiology is suspected and gradient between the deep and superficial venous systems is demonstrated.

3) During vasospasm cf cerebral arteries to maintain mean capillary pressure and/or to terminate vasospasm.

4) After stroke to prevent local veins collapse caused by a perifocal brain swelling.

5) In all other conditions, when control of venous outflow and mean capillary pressure can be beneficial.

We claim:

1. A method of detecting and treating cerebral blood vessel collapse, which comprises the steps of:

(a) changing pressure in a cerebral venous tract, and (b) detecting presence or absence of the vascular collapse by lowering pressure in the cerebral venous outflow tract and assessing intracranial pressure response so that if said response is registered as a comparable drop in intracranial pressure there is no venous collapse and if said response is not registered as a comparable drop in intracranial pressure the venous collapse is present, and (c) raising jugular vein bulb pressure to detect the point at which intracranial pressure begins to increase and measuring pressure gradient between intracranial cavity and jugular bulb at that point, and (d) lowering venous pressure up to the point at which intracranial pressure begins to drop and measuring pressure gradient between intracranial cavity and jugular bulb at that point, and (e) estimating a safe operating pressure gradient between intracranial cavity and jugular bulb as a gradient when small changes in jugular bulb pressure do not affect intracranial pressure, whereby presence of intracranial vascular collapse is detected and safe operating pressure gradient between intracranial cavity and jugular bulb is estimated which allows to control venous outflow pressure without affecting intracranial pressure thus enabling to restore cerebral blood flow through the collapsed vascular segments during intracranial pressure elevation.

2. The method according to claim 1 wherein cerebral vasospasm is terminated by raising cerebral venous outflow pressure to a level sufficient to open precapillary sphincters and thereafter returning venous outflow pressure to the baseline and repeating the same procedure, if necessary, until cerebral vasospasm is terminated.

3. The method according to claim 1 wherein the lowering of pressure in the cerebral venous outflow tract is achieved by withdrawing the blood.

\* \* \* \* \*